United States Patent [19]

McDaniel et al.

[11] Patent Number: 5,236,416

[45] Date of Patent: Aug. 17, 1993

[54] SYRINGE PLUNGER POSITION DETECTION AND ALARM GENERATION

[75] Inventors: John D. McDaniel, El Cajon; James E. Gharib, San Diego, both of Calif.

[73] Assignee: IVAC Corporation, San Diego, Calif.

[21] Appl. No.: 704,356

[22] Filed: May 23, 1991

[51] Int. Cl.$^5$ .................................. A61M 31/00
[52] U.S. Cl. .................................. 604/67; 604/155; 128/DIG. 1
[58] Field of Search ............ 604/65, 67, 151, 154–155, 604/245; 128/DIG. 1

[56] References Cited

U.S. PATENT DOCUMENTS

| | | |
|---|---|---|
| 3,235,220 | 2/1966 | Rantsch et al. . |
| 3,623,474 | 11/1971 | Heilman .................. 604/67 X |
| 3,757,591 | 9/1973 | Taylor . |
| 3,842,690 | 10/1974 | Gulick . |
| 3,858,581 | 1/1975 | Kamen . |
| 3,886,938 | 6/1975 | Szabo et al. . |
| 4,023,431 | 5/1977 | Pavlas . |
| 4,125,049 | 11/1978 | Price, Jr. . |
| 4,191,187 | 3/1980 | Wright . |
| 4,399,712 | 8/1983 | Oshikubo et al. .......... 73/864.16 |
| 4,424,720 | 1/1984 | Bucchianeri . |
| 4,435,173 | 3/1984 | Siposs et al. . |
| 4,465,474 | 8/1984 | Mardorf . |
| 4,544,369 | 10/1985 | Skakoon et al. . |
| 4,560,979 | 12/1985 | Rosskopf . |
| 4,620,848 | 11/1986 | Sutherland et al. ........... 604/154 |
| 4,685,903 | 8/1987 | Cable et al. . |
| 4,767,406 | 8/1988 | Wodhom et al. ............ 604/155 |
| 4,804,368 | 2/1989 | Skakoon . |
| 4,838,857 | 6/1989 | Strowe et al. ............... 604/67 |
| 4,908,017 | 3/1990 | Howson et al. . |
| 4,919,650 | 4/1990 | Feingold et al. . |
| 4,931,041 | 6/1990 | Faeser ....................... 604/155 |
| 4,952,205 | 8/1990 | Mauerer et al. ............... 604/67 |
| 4,959,056 | 9/1990 | Dombrowski et al. . |
| 4,976,696 | 12/1990 | Sanderson et al. ........... 604/154 |
| 4,988,337 | 1/1991 | Ito . |
| 5,006,112 | 4/1991 | Metzner . |
| 5,034,004 | 7/1991 | Crankshaw ................. 604/154 |

FOREIGN PATENT DOCUMENTS

| | | |
|---|---|---|
| 0354852 | 2/1990 | European Pat. Off. . |
| 3314664C2 | 2/1985 | Fed. Rep. of Germany . |
| WO90/10468 | 9/1990 | PCT Int'l Appl. . |
| 1475673A1 | 4/1989 | U.S.S.R. . |
| 2224444 | 5/1990 | United Kingdom ........... 604/155 |

Primary Examiner—C. Fred Rosenbaum
Assistant Examiner—Corrine Maglione
Attorney, Agent, or Firm—Fulwider, Patton, Lee & Utecht

[57] ABSTRACT

A syringe plunger position detection and alarm system continuously determines the position of a syringe plunger and provides near end of travel and end of travel alarms. Plunger movement is also monitored and if movement is less than a calculated amount, an alarm is provided. A variety of syringes of different sizes is usable. A potentiometer is mounted along the line of travel of the screw drive mechanism and a marker is mounted to extend from the screw mechanism to the potentiometer to force an internal contact in the potentiometer. The voltage provided by this internal contact is analyzed by the process to derive absolute and relative position of the plunger. The end of travel position of each plunger is stored in processor memory and from the operator input rate of infusion, the characteristic curve of the potentiometer also stored in memory, the plunger displacement of the syringe, and the time of the near end of travel alarm, the voltage of the near end of travel position is calculated. The potentiometer is self-contained and sealed.

28 Claims, 8 Drawing Sheets

SYRINGE PLUNGER POSITION DETECTION AND ALARM GENERATION

BACKGROUND OF THE INVENTION

The invention is related generally to a system for position determination and, more particularly, it is related to a system for determining the position of a syringe plunger and for providing an alarm upon the plunger reaching a selected position.

The infusion of fluids such as parenteral fluids into the human body is accomplished in many cases by means of a syringe pump having a lead screw on which a screw drive mechanism is mounted for translating the rotational motion of the lead screw into linear motion. A syringe plunger driver is connected to the screw drive mechanism for forcing the syringe plunger into the syringe barrel to expel the syringe contents at a desired rate. Because syringes having different sizes exist and syringes may be filled to different levels with infusion fluids, the extension of the plunger form the syringe barrel will differ from syringe to syringe. As a result, some screw drive mechanisms have a disengagement feature which the operator uses to disengage the screw drive mechanism from the lead screw, move the screw drive mechanism and plunger driver along the lead screw to the position of the new syringe plunger, engage the syringe plunger and then reengage the threads of the screw drive mechanism with the threads of the lead screw. Thus, the beginning position of the syringe plunger in relation to the lead screw will vary from syringe to syringe.

Likewise, the unextended or end-of-travel positions of the plungers in relation to the lead screw sill vary. Different syringes have different plunger extensions from the syringe barrel when the plunger has been fully driven into the syringe barrel and the syringe is empty. This distance is typically measured between the syringe barrel flange and the plunger flange and this extension distance varies between syringes of different sizes and also between syringes from different manufacturers. As a consequence, many pumps are designed to work only with one syringe from one manufacturer. This greatly reduces the value of the pump. If that particular syringe is not available, the pump is unusable.

In some syringe pumps, a split nut or half nut or other mechanism is used as part of the lead screw drive mechanism to selectively engage the lead screw. A linkage mechanism rigidly links the split nut to the syringe plunger driver, and because of this, the position of the syringe plunger can be determined from the position of the split nut or from other locations on the linkage.

In some syringe plunger position determination devices, the position of the plunger is determined by monitoring the number of revolutions that the lead screw rotated. A set of gears transmitting force from the motor to the lead screw is sued and the rotation of one of these gears is monitored. A disadvantage of this technique is the failure to monitor the actual device directly causing the syringe plunger movement, the plunger driver. In this technique, the monitored gear may turn regardless of the state of operation of the plunger drive. In the case where the threads of the lead screw are stripped or broken, no motion of the plunger driver may actually occur although the monitored gear turns. In such a situation, the patient may receive no infusion fluid until the pump operator notices that the contents of the syringe have not decreased.

In other pumps, markers at fixed positions along the travel of the plunger driver are used. These may be optical markers and are read by a detector on the plunger driver. Other systems have been used, including magnetic and inductive systems. However, in most of these systems, only relative position information concerning the plunger driver is available. The system can determine how far the plunger driver has moved but cannot determine where it is in relation to a fixed position, such as its end of travel or unextended position.

In another syringe plunger position device, an electric contact is made between the movable syringe plunger driver and a stationary linear potentiometer by way of an electrically conductive wiper mounted on the plunger driver. The position of the syringe plunger is then ascertained by comparing the voltage of the wiper to other voltages across the potentiometer. The wiper voltage is proportional to the position of the syringe plunger. This approach, however, has the disadvantage of having an exposed electrical contact at the wiper which can accumulate contaminants and degrade performance. Sealing the wiping contact is difficult due to its connection to the plunger driver and the relatively long distance it moves.

In addition, it is believed by the inventor that the above approaches have not provided a means to accept various sizes of syringes with their differing plunger travel distances and the differing positions of their plungers when unextended from the syringe barrel.

Hence those skilled in the art have recognized a need for a more accurate, versatile and reliable plunger position determination system. The present invention fulfills that need.

SUMMARY OF THE INVENTION

Briefly, and in general terms, the present invention resides in a new and improved apparatus and method for determining the absolute and relative positions of the moving plunger of a syringe, the syringe selected from a plurality of different syringes all of which are specified for the same pump. Determinations are made as to when the plunger has reached preselected positions in its travel. One position is the end-of-travel position at which the plunger is fully driven into the syringe barrel. Another position is a near end-of-travel position at which the plunger has some time remaining before reaching the end of-travel position. This is typically a position at which three minutes are remaining. Alarms are provided at these positions. In yet another feature, movement of the plunger driver itself is monitored to determine relative position to check for pump failure.

In accordance with one aspect of the invention, a mechanical, non-electrical connection is made between the movable syringe plunger driver and a stationary potentiometer. The plunger driver engages the syringe plunger to cause its movement relative to the syringe barrel. In one embodiment, the potentiometer is sealed and self-contained in that it contains its own internal wiping contact which is activated by sufficient external mechanical pressure to cause contact between two internal surfaces. A processor contains data relating to the particular syringe in use which includes the end-of-travel position of the plunger of that syringe. The data also includes the volume per distance (milliliters/inch) characteristic of the syringe.

A processor receives the operator's indication of the installed syringe type and the selection of infusion rate and calculates the rate of plunger movement to obtain that infusion rate with that syringe. The processor also determines the end-of-travel voltage to be received from the potentiometer wiping contact which would indicate the end-of-travel position for this syringe. To perform this calculation, the processor recalls the stored end of travel position for the particular syringe and the particular response characteristic for the potentiometer, which may not be linear. The processor also determines the voltage for the near end-of-travel point, which in one embodiment is fixed at three minutes. The processor then periodically monitors the continuous output voltage from the potentiometer wiping contact, compares it against the calculated near end-of-travel voltage and upon discovering equality, provides an alarm. The processor also provides an end-of-travel alarm when the wiping contact voltage equals the calculated end-of-travel voltage.

In accordance with another feature, data relating to a plurality of syringes having different sizes and manufacturers are stored in the processor so that it is possible to use a variety of different syringes in the pump and still have accurate near end-of-travel and end-of-travel alarms.

In another feature, the processor monitors the voltage change from the potentiometer wiping contact to determine the relative position of the plunger driver to determine plunger driver movement. In the event that the voltage does not change according to the infusion rate selected by the operator, the processor provides an alarm. Because the plunger driver itself is mechanically linked to the potentiometer, a reliable plunger movement detector is provided.

Other aspects and advantages of the invention will become apparent from the following detailed description and the accompanying drawings, illustrating by way of example the features of the invention.

DETAILED DESCRIPTION OF THE PREFERRED EMBODIMENTS

Figure 1:
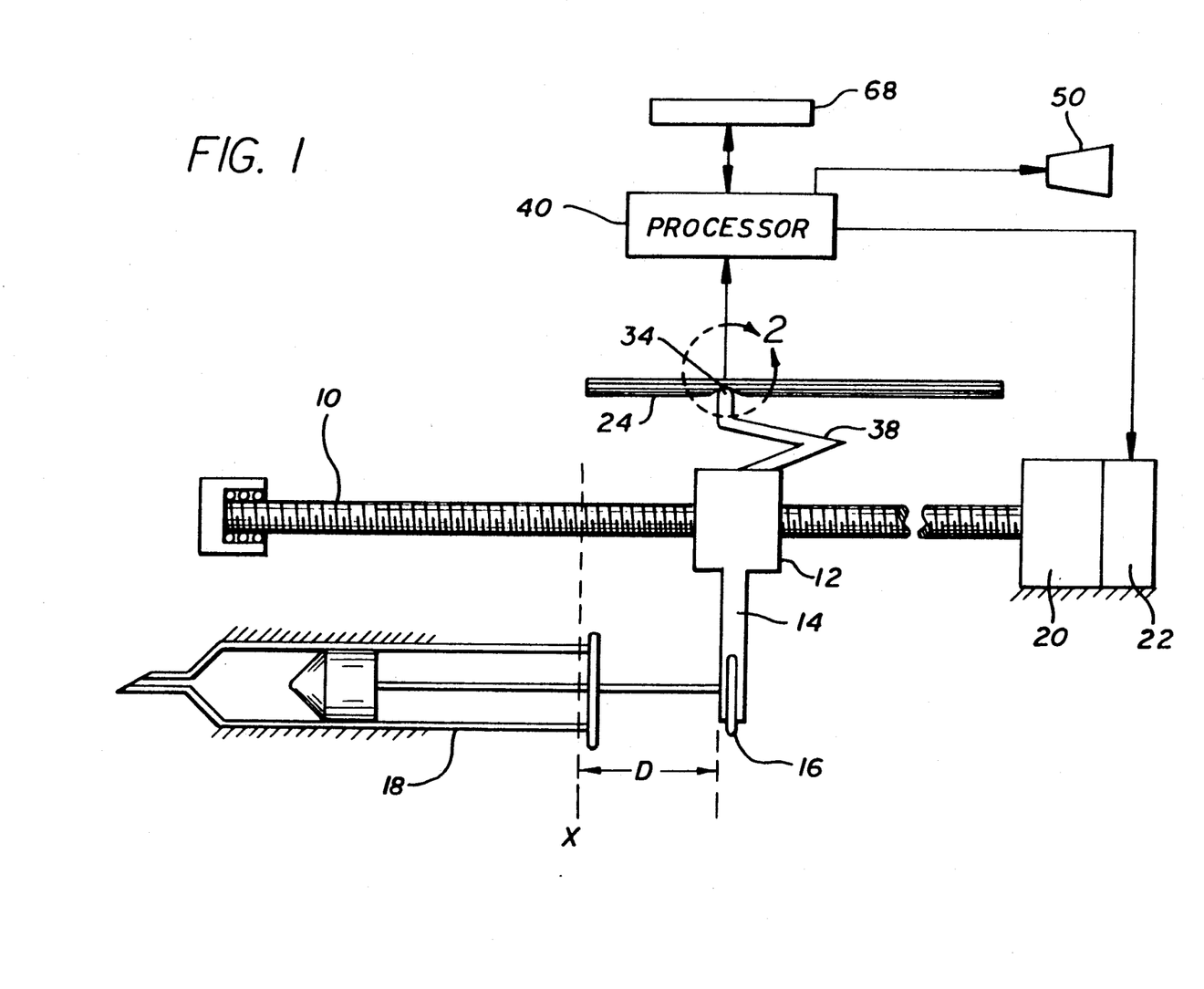
FIG. 1 presents a block diagram of a plunger position detection system in accordance with the principles of the invention.

Referring now to the drawings with more particularly, wherein like reference numerals designate like or corresponding elements among the several views, there is shown in FIG. 1 a lead screw 10 engaged by a moveable screw drive mechanism 12 that is connected by a plunger driver 14 to plunger 16 of syringe 18. The screw drive mechanism 12 could be of the half-nut or split-nut design, as is known in the art. The threaded lead screw 10 supplies rotational motion that is translated to linear motion by the screw drive mechanism 12. Plunger driver 14 holds the plunger 16 of the syringe 18. The rate of rotation of the motor 20, controlled by a suitable motor control 22, determines the rate of linear movement of the plunger driver 14.

The position of the screw drive mechanism 12, which moves the plunger driver 14 and the plunger 16, is sensed by means of a potentiometer 24. The potentiometer 24 is stationary and extends along the lead screw through the range of travel of the screw drive mechanism 12. In one embodiment, the potentiometer extends from the point representative of a plunger fully driven into its syringe barrel and having a minimum extension between the plunger flange and the barrel flange to the point representative of the position that the longest plunger of a syringe specified for the pump would be in if fully extended.

Figures 2, 3:
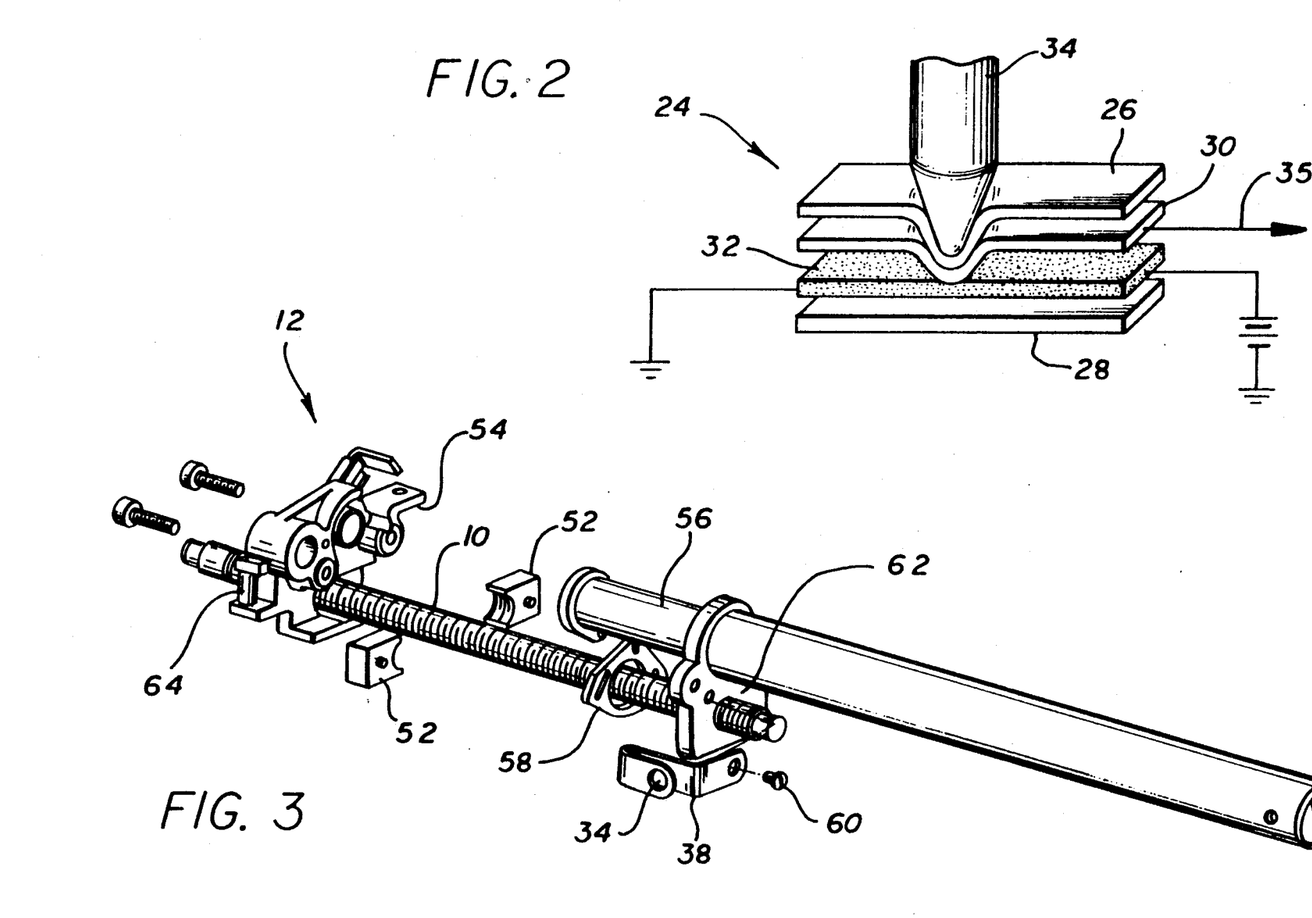
FIG. 2 presents a perspective, cross-sectional view of a self-contained, sealed potentiometer used in FIG. 1.
FIG. 3 presents an exploded view of a screw drive mechanism showing the mounting of the marker and spring bias.

Referring now to FIG. 2, the potentiometer 24 comprises four parallel layers, the two outside layers 26 and 28 being insulative or protective in nature and electrically non-conducting. One inside layer is a shorting layer 30 and the other inside layer 32 is a resistive layer. The shorting layer 30 operates similarly to a wiper on a potentiometer having moving parts except that it does not move along the resistive layer 32 but only moves into and out of contact with it when pressed by an outside mechanical force. For purposes of convenience, it is referred to herein as the wiping contact. A power source $V_b$ is shown applying power to the resistive layer 32.

A marker 34 pressing against the shorting layer 30 with enough force will cause the shorting layer 30 to contact the resistive layer 32 and a voltage $V_o$ will be developed at the contact point. The voltage developed $V_o$ will be somewhere between the voltage $V_b$ residing across the resistive layer 32 and the ground potential. Based on the voltage $V_o$ developed by the shorting layer and provided at the output terminal 35, the exact physical position of the contact between the shorting and resistive layers can be determined. In the case shown in FIG. 2, if the voltage at the terminal 35 is $V_b$, the point of contact will be determined to be at the rightmost side of the potentiometer 24. If the voltage at terminal 35 is ground, the point of contact will be determined to be at the leftmost side. The voltage will vary between these two extremes to indicate the point of contact, although it may not vary linearly. Other embodiments for applying power to the potentiometer 24 are possible. For example, in FIG. 2, ground may be the high potential and a negative voltage the low potential.

Referring again to FIG. 1 with FIG. 2, the device pressing against the potentiometer in this embodiment is a position reference marker 34 which is biased against the potentiometer 24 by a leaf spring 38. This leaf spring 38 is mounted to the screw drive mechanism 12 and moves with it. Other spring types are usable as well as other means of pressing the marker 34 against the potentiometer. As a consequence of this mechanical linkage, the physical position of the plunger 16 can be determined based on the output voltage V measured across the resistive and shorting layers and accessible at output terminal 35. The spring force against the potentiometer 24 is selected to apply enough force to cause an electrical contact between the resistive layer 32 and the shorting layer 30. Such a potentiometer is available from Spectra Symbol having an address of 2534 Directors Row, Salt Lake City, Utah and known as the SOFT-POT. this particular potentiometer has a force requirement of six to twenty ounces (170 to 567 grams) to cause internal contact. The output voltage $V_o$ from the output terminal 35 of the shorting layer 30 is input to a processor 40.

Referring now to FIG. 3, an exploded view of the mechanical connection between a leaf spring 38 with an integral marker 34 and a screw drive mechanism 12 is shown. The screw drive mechanism 12 includes a split nut 52 for threadably engaging the lead screw 10. The split nut 52 is contained in a nut housing 54 and a drive tube 56 connects the plunger driver 14 (not shown) to the split nut through a cam plate 58. A screw 60 attaches the leaf spring 38 to a part of the lead screw housing 62. The bend of the spring 38 is positioned through a spring support rod 64 which is mounted in the housing 54. Thus, the spring 38 and integral marker 34 move with the screw drive mechanism 12.

Figure 4:
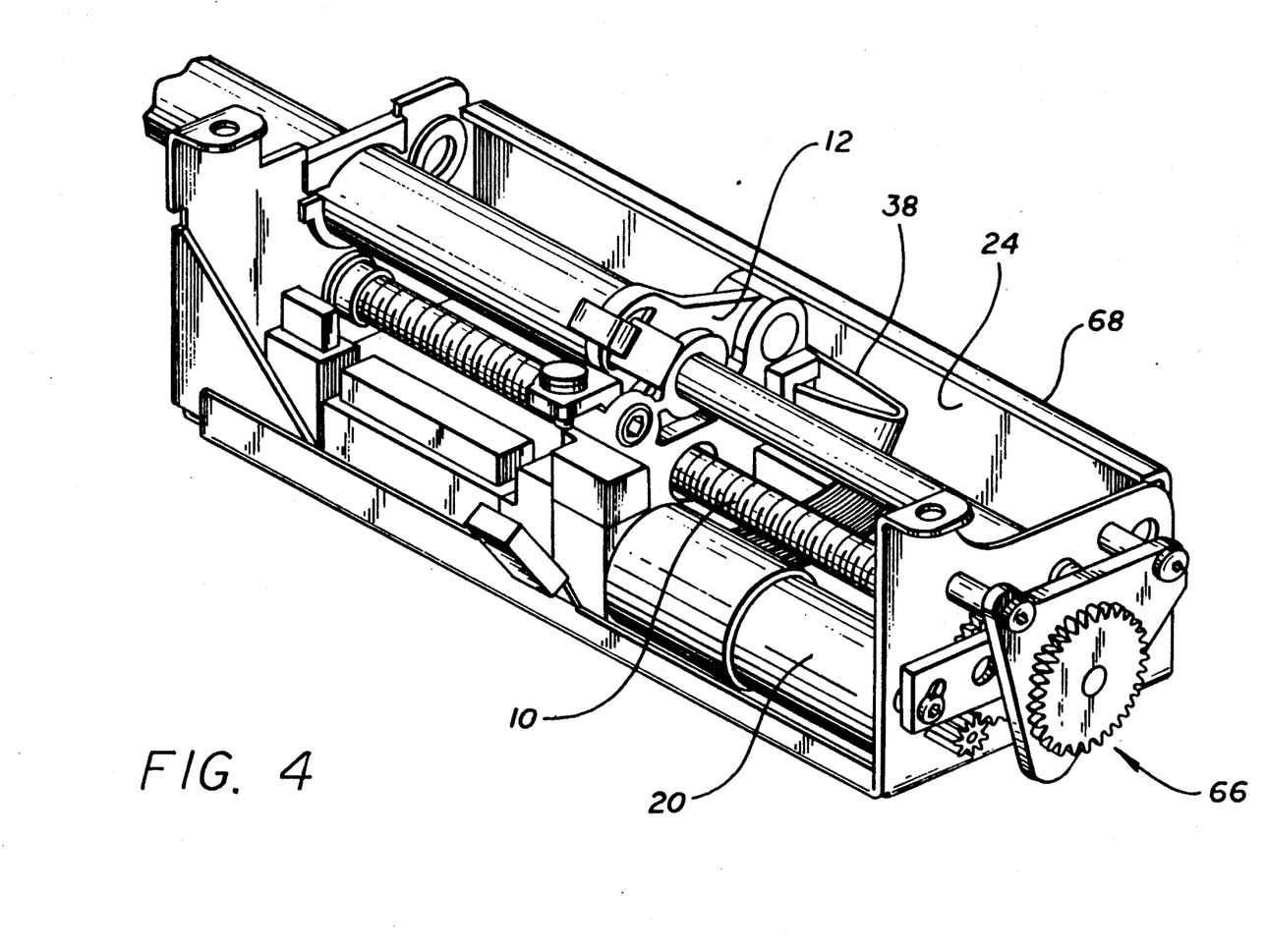
FIG. 4 presents a partial assembly drawing of the location of the potentiometer in relation to the lead screw and screw drive mechanism in a syringe pump.

Referring now to FIG. 4, the position of the mechanism shown in FIG. 3 in a syringe pump assembly is shown. A back view of part of the pump assembly is shown wherein the pump motor 20 is connected to the lead screw 10 through a set of gears 66 at the end of the assembly. The screw drive mechanism 12 is engaged with the lead screw 10 and the potentiometer 24 is mounted to the inside of the front of the pump housing 68. The spring 38 causes the marker 34 to press against the potentiometer as the screw drive mechanism 12 moves along the lead screw 10.

It is significant to note that the only connection between the plunger driver 14 and the potentiometer 24 is a mechanical one and the processor 40 and the potentiometer 24 do not form an electrical circuit with the position reference marker 34. Also, the potentiometer 24 is sealed thus avoiding the possible degradation of performance caused by dirt and other contaminants attaching themselves to a wiper as in other devices. In this way, the possibility of exposure of the wiper to outside elements, and concomitant contamination and the possibility of an open circuit occurring at the interface between the position reference marker 34 with the potentiometer 24 is eliminated. No electrical power is placed on the screw drive mechanism 12 nor on the plunger driver 14 or plunger 16 as a result of the position determination system.

Figure 5:
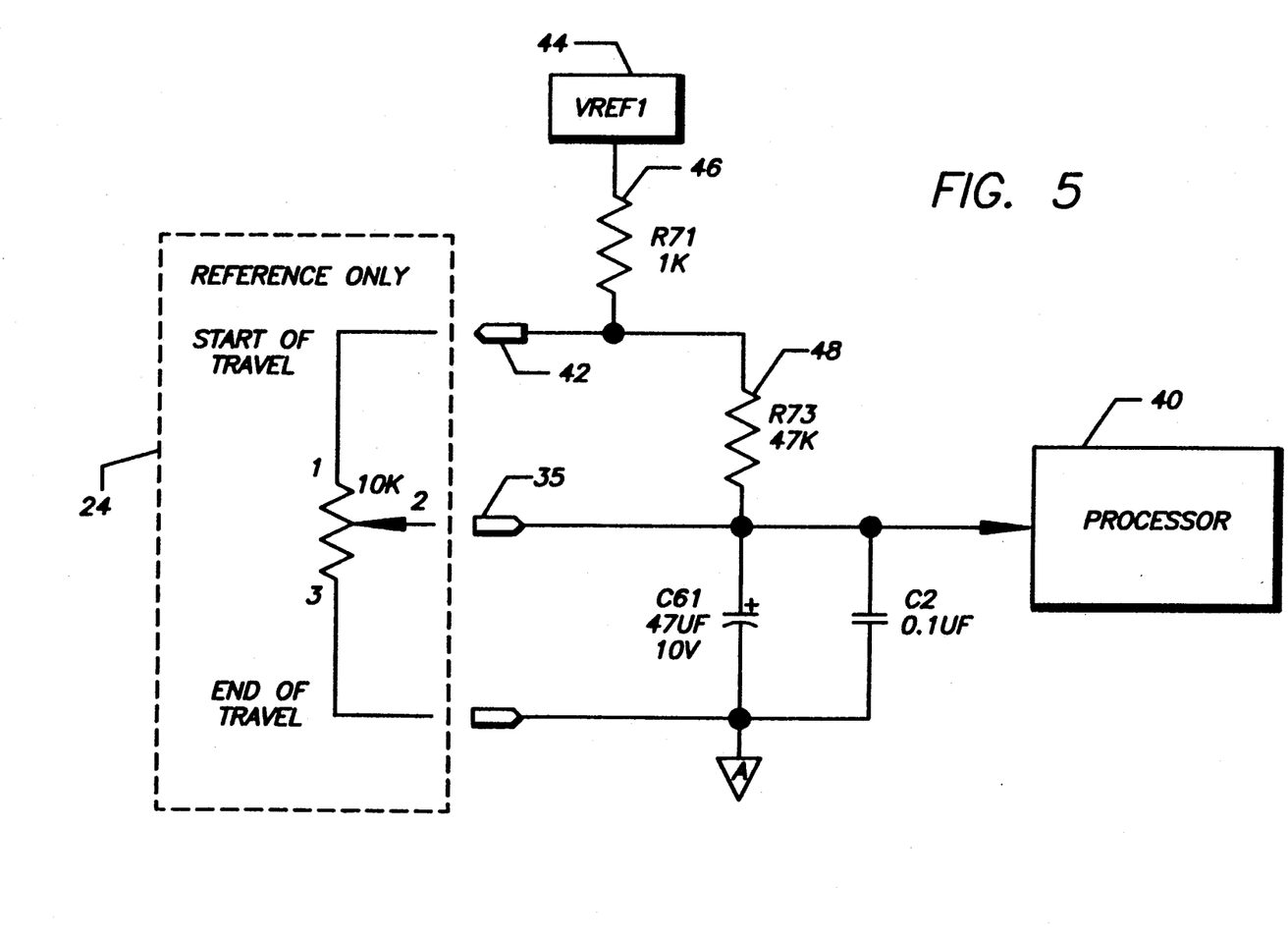
FIG. 5 presents a block diagram of an electrical circuit which couples the potentiometer to the processor.

Referring now to FIG. 5, a circuit is shown which connects the potentiometer 24 to the processor 40 and provides compensation for the possibility of a short or open circuit in the potentiometer 24. One end of the resistive layer 32 has a terminal 42 and is connected to a voltage source 44 through a current limiting resistor 46. The output of this terminal 42 is also connected to the shorting layer output 35 through a second resistor 48. The second resistor 48 is large compared to the total resistance across the potentiometer 24, in this case a 47kΩ resistor 48 compared to a 10kΩ potentiometer 24, and in the event that the potentiometer 24 fails and becomes a short circuit, this resistor 48 will result in the wiping contact showing little or no voltage to the processor 40. The processor 40 will interpret this as the plunger having reached the end of travel position and will stop pump movement and provide an alarm.

If potentiometer 24 pin 1 fails to an open circuit, the wiping contact will provide a slow moving low voltage to the processor 40. The processor 40 will interpret this as the plunger moving too slow per unit time and will stop pump movement and will provide an alarm. If potentiometer 24 pin 2 fails to an open circuit, the wiping contact will provide a fixed high voltage to the processor 40. The processor 40 will interpret this as the plunger not moving and will stop pump movement and provide an alarm. If potentiometer 24 pin 3 fails to an open circuit the wiping contact will provide a fixed high voltage to the processor 40. The processor 40 will interpret this as the lunger not moving and will stop pump movement and provide an alarm.

Figure 6:
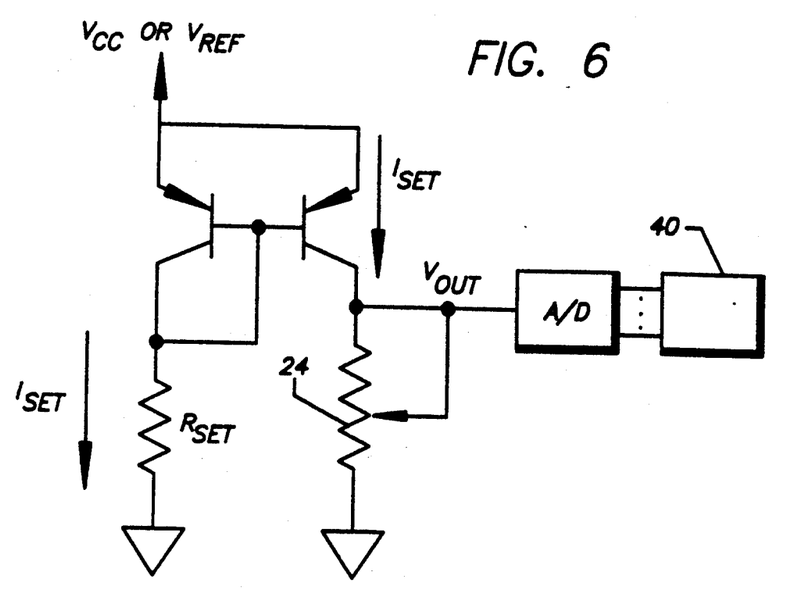
FIG. 6 presents a schematic diagram of a current source circuit usable with the potentiometer.
Figure 7:
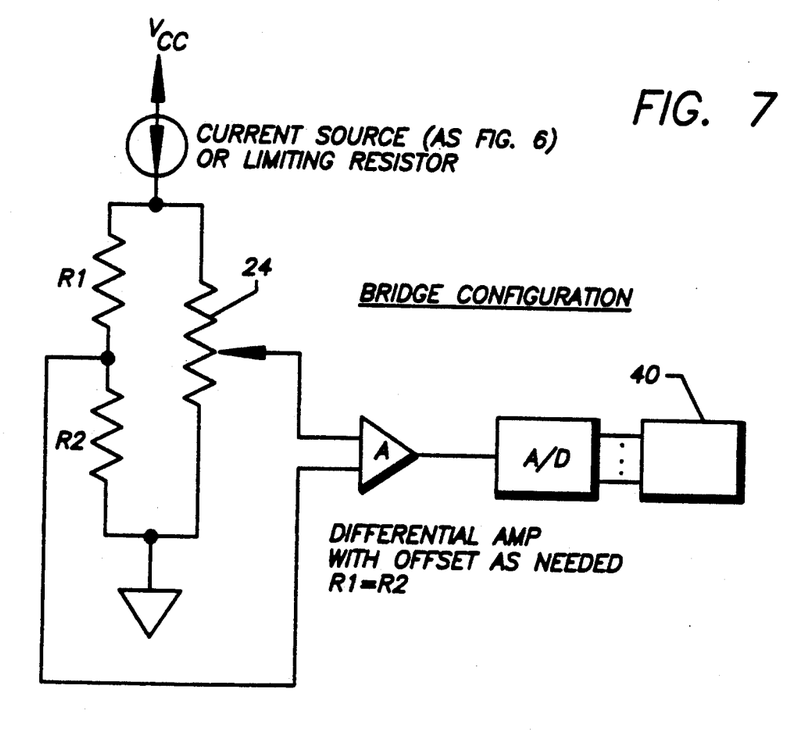
FIG. 7 presents a schematic diagram of a bridge circuit usable with the potentiometer.

Other implementations of a potentiometer 24 and processor interface are possible. For example, a current source as shown in FIG. 6 may be used with the potentiometer. In another example, a bridge circuit as shown in FIG. 7 may be used.

Additionally, although not shown, the processor may contain other interface devices well known in the art such as a multiplexer and an analog-to-digital converter for processing the potentiometer signal.

Referring again to FIGS. 1 and 5, in the event that the potentiometer 24 provides an end of travel signal to the processor 40, the processor will provide an alarm 50 which may be visible and/or audible. When the screw drive mechanism 12 and plunger driver 14 are engaged with a full syringe plunger, the potentiometer 24 will output a relatively high voltage. As the plunger driver proceeds to empty the syringe 18, the voltage will decrease until it reaches the end of travel (EOT) position of the syringe plunger.

In accordance with one aspect of the invention, the processor 40 includes pre-stored data representative of the end of travel positions of all syringes specified for the pump. A reference position "X" is established along the lead screw travel from which the end of travel positions of all syringes specified for the pump are measured. After the operator specifies to the processor 40 the syringe being used, the processor 40 calculates the voltage that the potentiometer 24 output terminal 35 will provide to indicate that the plunger has arrived at the end of travel position. This calculation will take into account the response characteristics of the potentiometer 24 which may not be linear and which are also stored in the processor 40. Upon start of the pumping process, the processor 40 continuously monitors the voltage from the potentiometer 24 and upon determining equality of the potentiometer 24 voltage with the calculated end of travel voltage for that particular syringe, provides the alarm 50. The pump operator may input to the processor 40 a code identifying the particular syringe in use by means of a keypad 67 or other means. In another embodiment, automatic detection of the syringe type may be provided.

Additionally, the processor 40 may be used to determine a fixed or selectable near end of travel (NEOT) position of the syringe plunger. In many cases, the pump operator desired to have an alarm provided three minutes before the syringe is empty. This would enable the pump operator or other personnel to prepare another syringe or perform other necessary actions. Thus, the processor would need to translate the three minute near end of travel position into a potentiometer voltage. The processor would have received the rate of infusion from operator input and would have calculated the end of travel voltage from pre-stored data. The processor will then calculate the three minute near end of travel point.

In order to calculate a near end of travel position corresponding to a selected time remaining in the syringe, the processor 40 must be programmed with a variety of variables and, in addition, must receive data measuring during infusion. Some of the programmed values and measured data include: the voltage provided by the potentiometer output terminal 35; the volume per distance of plunger movement (milliliters/inch) characteristic of the syringe; the end-of-travel position associated with this syringe; the time before end of travel for the near end-of travel alarm NEOT; and the characteristic curve of voltage versus position for the potentiometer 24.

Variables that can be pre-stored in the processor include the characteristic curve of voltage versus position for the particular potentiometer 24, which may or may not be linear; the volume per distance of plunger movement (milliliters/inch) of all the syringes specified for the pump and the end of travel positions of all of the syringes. These "syringe particular" variables may be data stored in the processor memory and called up upon the operator identifying the particular syringe in use by the keypad 67.

As one example of determining the end of travel voltage, the processor would perform the following calculation:

$$\text{threshold voltage } (EOT) = \frac{\text{position}}{\text{calibration slope}} + \text{calibration offset}$$

where "position" is in inches and the calibration terms are in volts per inches.

A similar calculation is used by the processor to determine the voltage for the three minute warning as follows:

threshold voltage $(NEOT) =$ $$\text{threshold voltage } (EOT) + \frac{\text{infusion rate} \times \text{warning time}}{(\text{syring vol. rate})}$$

where the syringe volume rate is typically in ml/inch.

Additionally, in one embodiment, the processor will include hysteresis feature. In accordance with this feature, once the threshold voltage is received by the processor from the potentiometer, the alarm will be given and will be maintained unless a subsequent movement into a non-alarm condition occurs which is greater than the movement into the alarm condition. This feature aids in avoiding false alarms which may occur due to noise induced plunger movement.

Figure 8:
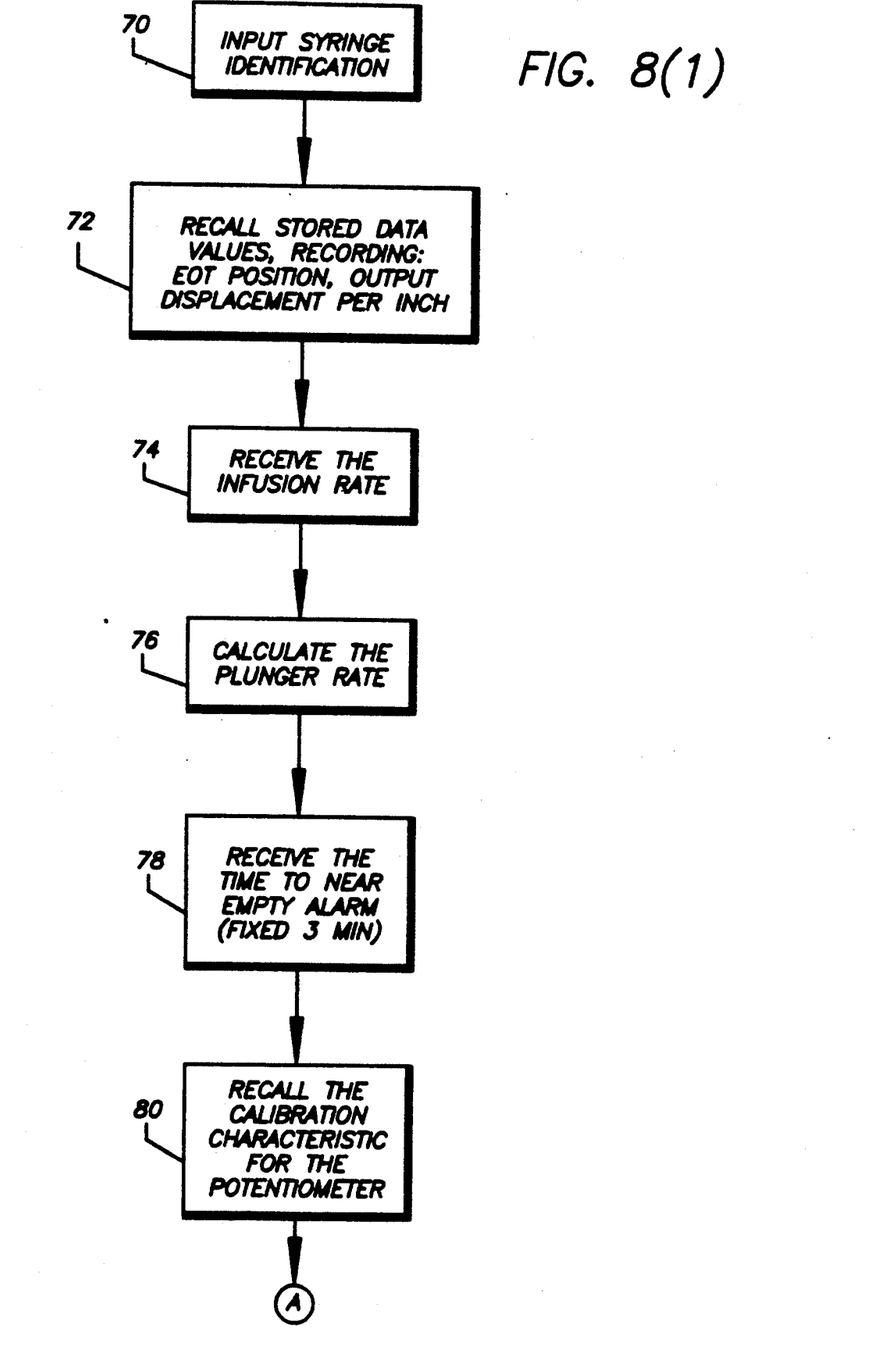
FIG. 8 presents a flow chart of a method in accordance with the principles of the invention.

Referring now to FIG. 8 which presents a flow chart of an embodiment of position detection and alarm generation in accordance with the invention, the operator would identify the particular syringe in use 70 and in response, the processor 40 would recall 72 the stored data relating to that syringe. This data comprises EOT position and output displacement of the syringe, typically in ml/inch. The operator would also input the infusion rate desired 74 from which the processor would calculate the plunger rate of movement 76. The processor 40 then recalls the fixed near end of travel alarm time 78, and recalls stored data 80 relating to the characteristic curve of the potentiometer and circuitry associated therewith and calculates 82 the voltage change per unit time, the voltage at the NEOT point and the voltage at the EOT point.

In calculating the amount of change in voltage per unit of time, which is related to a unit of movement of the plunger, the processor may consider the resolution of the potentiometer, the accuracy and tolerances, and desired false alarm rate in setting the threshold change in voltage to be monitored.

The processor monitors 83 any operator change in the infusion rate or the syringe selected. The processor 40 then determines if three minutes have expired from the three minute alarm. If the three minutes have elapsed, the pump movement is stopped 84.

The processor then monitors 85 the voltage of the potentiometer and determines if the voltage is changing per unit of time 86. If the potentiometer voltage does not change by the calculated amount, the pump is stopped 87 and an alarm given 88. In one embodiment, the processor provides the alarm if the change is too great, too little or is negative. The processor also simultaneously monitors for the near end of travel voltage 90. Upon sensing the NEOT voltage, the processor starts a three minute timer 92 and provides the NEOT alarm 94. The processor also simultaneously monitors for the end of travel voltage 96 and if sensed, stops the pump 84 and provides an alarm 98. If not sensed, the pump operation continues 83.

In this embodiment, the processor 40 periodically samples the voltage of the potentiometer 24 at a sample rate of every 200 to 300 milliseconds. However, the output of the potentiometer 24 is continuous, therefore the processor sampling rate may be changed.

The operator can change 83 the rate of infusion and/or the desired warning time through the keypad 67 during pump operation in which case the processor 40 will recalculate 82 the near end of travel voltage and change in voltage per unit time.

In one embodiment in sensing voltage change, the processor looks for 86 a certain voltage change for each 0.2" (5.1 mm) of travel of the plunger per unit of time. If the voltage change has not occurred in the unit of time, the processor determines that the plunger is not moving as required and provides the alarm 88.

Although specific embodiments of the invention have been described and illustrated it is clear that the invention is susceptible to numerous modifications and embodiments within the ability of those skilled in the art, and without the exercise of the inventive faculty. Thus, it should be understood that various changes in form, detail and application of the present invention may be made without departing from the spirit and scope of the invention.

We claim:

1. An apparatus for determining the position of a plunger of a syringe, comprising:

a position marker coupled to and moving with said plunger;

stationary detector means, said position marker means being coupled mechanically and non-electrically to said stationary detector means for linear movement relative thereto, said stationary detector means for providing a position signal in response to said linear movement of said position marker relative to said stationary detector means, said position signal differing for different positions of said position marker along said stationary detector means; and processor means for receiving said position signal and for determining an absolute position of the plunger in response thereto, said processor means monitoring said position signal over a pre-determined unit of time, comparing said received position signals, and based on said comparison, determining if movement of the said drive means is occurring.

2. The apparatus of claim 1, wherein said syringe plunger has a starting position and an end of travel position, and wherein said processor means comprises:
   memory means in which position data is stored relating to the end of travel position;
   means for calculating a signal to be received from said stationary detector means which would indicate the end of travel position; and
   means for generating an end of travel alarm when said processor means receives a position signal from said stationary detector means which equals said calculated end of travel position signal.

3. The apparatus of claim 1, further including means for receiving a plurality of differently sized syringes, and wherein said processor means comprises:
   memory means containing data related to each of the syringes, the data including position data relating to an end of travel position for the plunger of each said syringe;
   means for calculating a position signal to be received from said stationary detector means which would indicate the end of travel position for a selected one of said syringes; and
   means for generating an end of travel alarm when said processor means receives a position signal from said stationary detector means which equals said calculated position signal indicating said end of travel.

4. The apparatus of claim 1, wherein said syringe plunger has a starting position and an end of travel position, and wherein said processor means further comprises means for calculating a signal to be received from said stationary detector means which would indicate a selected position between the starting position and the end of travel position, and means for providing a selected position alarm when said processor means receives a position signal from said stationary detector means which equals said calculated position signal.

5. The apparatus of claim 1, wherein said stationary detector means comprises a potentiometer and said position marker means is resiliently biased against said potentiometer.

6. The apparatus of claim 5, wherein said potentiometer provides said position signal to received by said processor means, and said position signal is a voltage signal.

7. The apparatus of claim 1, further including means for inputting a desired rate of movement of said syringe plunger into the processor, and wherein said processor means includes means for calculating a desired rate of change in the position signal over time which would occur at the desired rate, means for comparing the change in the position signal to the calculated rate of change of the position signal, and means for providing an alarm if the change in the position signal differs from the calculated desired rate of change signal.

8. The apparatus of claim 7, wherein said position signal is a voltage signal, said desired rate of change in the position signal is a minimum change in voltage over time, and said means for providing an alarm operates to provide an alarm if the change in voltage of said position signal is less than said minimum change in voltage over time.

9. The apparatus of claim 1 wherein the stationary detector comprises a linear potentiometer disposed along a predetermined length of and in parallel with the route of travel of the position marker.

10. A plunger position determination apparatus for determining the position of a plunger which is disposed within an enclosure, said plunger having an end of travel position at which it is driven into the enclosure to a predetermined position and a starting position at which it is in a retracted position in the enclosure, the apparatus comprising:
   a plunger driver coupled to the plunger and moving the plunger from the starting position to the end of travel position;
   a position marker fixedly coupled to and moving with said plunger driver;
   a stationary detector mechanically and non-electrically coupled to the marker and which provides a position signal in response to said coupling, the position signal being different for different coupling positions of the marker along the detector, the position signal changing in response to movement along the detector; and
   a processor which receives the position signal and determines the absolute position of the marker in response thereto, and which receives position signals over a predetermined unit of time from the detector and determines if movement of the plunger driver is occurring.

11. The apparatus of claim 10 wherein the processor:
   includes a memory in which is stored position data relating to the end of travel position of the plunger;
   calculates a signal to be received from the detector which would indicate the end of travel position; and
   upon receiving a position signal from the detector which equals the calculated end of travel position signal, provides an end of travel alarm.

12. The apparatus of claim 10 for determining the position of the plunger selected from a plurality of plungers specified for the apparatus, said plurality of plungers having different end of travel positions, wherein the processor includes a memory containing data related to each of the plungers, the data including position data relating to the end of travel position of each said plunger;
   the processor calculates a signal to be received from the detector which would indicate the end of travel position for that plunger; and
   upon receiving a position signal from the detector which equals the calculated position signal, provides an end of travel alarm.

13. The apparatus of claim 10 wherein the processor calculates a signal to be received from the detector which would indicate a selected position for the plunger between the starting position and the end of travel position; and
   upon receiving a position signal from the detector which equals the calculated position signal, provides a selected position alarm.

14. The apparatus of claim 10 wherein the detector comprises a potentiometer and said marker is resiliently biased against said potentiometer.

15. The apparatus of claim 14 wherein the potentiometer provides a voltage signal which is received by the processor.

16. The apparatus of claim 10 wherein the processor:
   receives a desired rate of movement of the plunger driver;

calculates a change in the position signal per unit of time which would occur at that rate;

compares the change in the position signal from the detector to that calculated rate of change of position signal and provides an alarm if the two differ.

17. The apparatus of claim 10, wherein at said end of travel position said plunger is fully driven into said enclosure.

18. The apparatus of claim 1 wherein the stationary detector comprises a linear potentiometer disposed along a predetermined length of and in parallel with the route of travel of the position marker.

19. An apparatus for determining the position of a drive mechanism, said drive mechanism including drive means for providing a movement force to the drive mechanism, and engagement means for engaging said drive mechanism and moving in response thereto, said engagement means being movable relative to said drive means, and, said element for determining position of a drive mechanism having:

a position marker fixedly coupled to and moving with said engagement means;

a stationary detector means mechanically and non-electrically coupled to said position marker for generating a position signal responsive to relative movement of said position marker with respect to said stationary detector means; and processor means for receiving said position signal and determining the absolute position of said position marker means relative to said stationary detector means responsive to said position signal, said processor means receiving position signals over a predetermined unit of time, comparing said position signals, and determining if movement of the said drive means is occurring based on said comparisons.

20. The apparatus of claim 19, wherein said drive mechanism has a starting position and an ending position, and wherein said processor means comprises:

memory means in which position data is stored relating to the ending position;

means for calculating a signal to be received from said stationary detector means which would indicate the ending position; and means for generating an ending position alarm when said processor means receives a position signal from said stationary detector means which equals said calculated ending position signal.

21. The apparatus of claim 19, wherein said drive mechanism has a starting position and an ending position, and wherein said processor means further comprises means for calculating a signal to be received from said stationary detector means which would indicate a selected position between the starting position and the ending position, and means for providing a selected position alarm when said processor means receives a position signal from said stationary detector means which equals said calculated position signal.

22. The apparatus of claim 21, wherein said ending position is an end of travel position.

23. The apparatus of claim 19 wherein said drive mechanism is a linear drive mechanism.

24. The apparatus of claim 19, wherein said stationary detector means comprises a potentiometer and said position marker means is resiliently biased against said potentiometer.

25. The apparatus of claim 24, wherein said potentiometer provides said position signal to be received by said processor means, and said position signal is a voltage signal.

26. The apparatus of claim 19, further including means for inputting a desired rate of movement of said drive means into the processor, and wherein said processor means includes means for calculating a desired rate of change in the position signal over time which would occur at the desired rate of movement, means for comparing the change in the position signal to the calculated rate of change of the position signal, and means for providing an alarm if the change in the position signal and the calculated desired rate of change signal differ.

27. The apparatus of claim 19, wherein said position signal has a voltage, and further including means for determining a change in voltage of said position signal over time; means for inputting a desired rate of change of voltage of said position signal into the processor; means for comparing said desired rate of change of voltage and said change of voltage; and means for providing an alarm if the change of voltage is less than said desired change of voltage.

28. The apparatus of claim 19 wherein the stationary detector comprises a linear potentiometer disposed along a predetermined length of and in parallel with the route of travel of the position marker.

* * * * *

UNITED STATES PATENT AND TRADEMARK OFFICE
CERTIFICATE OF CORRECTION

PATENT NO. : 5,236,416

DATED : August 17, 1993

INVENTOR(S) : John D. McDaniel, James E. Gharib

It is certified that error appears in the above-identified patent and that said Letters Patent is hereby corrected as shown below:

Title page,
   Column 2, Line 12 of the Abstract, change "process" to read --processor--.

In the drawings:

Fig. 2, insert --$V_o$-- at arrow 35.

Fig. 2, insert --$V_b$-- at the symbol for battery.

In the Background of the Invention:

Column 1, Line 22, change "form" to --from--.

Column 1, Line 35, change "sill" to --will--.

Column 1, Line 59, change "sued" to --used--.

Column 1, Line 64, change "drive" to --driver--.

Column 2, Line 28, change "inventor" to --inventors--.

UNITED STATES PATENT AND TRADEMARK OFFICE
CERTIFICATE OF CORRECTION

Page 2 of 4

PATENT NO. : 5,236,416
DATED : August 17, 1993
INVENTOR(S) : John D. McDaniel; James E. Gharib It is certified that error appears in the above-identified patent and that said Letters Patent is hereby corrected as shown below:

In the Summary of the Invention:
At Column 2, starting at Line 39 through Line 68, delete all text; further to Column 3, Line 1 through Line 35, delete all text and insert the following: --Briefly, and in general terms, the present invention resides in a new and improved position determination apparatus for determining the absolute position of a moving plunger in one aspect and a moving drive mechanism in another aspect. A stationary detector is mechanically and non-electrically coupled to a movable position marker and generates a position signal responsive to the movement of the marker. The position signal differs for different coupling positions of the marker along the detector and the position signal changes in response to movement along the detector. A processor receives the position signal and determines the absolute position of the marker in response to that received signal. The processor also receives position signals over a predetermined unit of time and determines if movement is occurring. The position marker is coupled to and moves with the plunger in one aspect, to the plunger driver in another aspect and to the engagement means in a further aspect.

In a further feature, the processor includes a memory in which is stored position data relating to the end of travel position or the ending position of the plunger or of the drive mechanism respectively. The processor calculates a signal to be received from the detector which would indicate the end of travel or ending position and upon receiving a position signal from the detector which equals the calculated position signal, the processor provides an alarm. In yet a further aspect, the processor includes a memory which contains data related to each of a plurality of plungers or syringes including position data relating to the end of travel position of each plunger.

UNITED STATES PATENT AND TRADEMARK OFFICE
CERTIFICATE OF CORRECTION

Page 3 of 4

PATENT NO. : 5,236,416

DATED : August 17, 1993

INVENTOR(S) : John D. McDaniel, James E. Gharib

It is certified that error appears in the above-identified patent and that said Letters Patent is hereby corrected as shown below:

In yet a further aspect, the processor calculates a signal to be received from the detector which would indicate a selected position for the plunger or drive mechanism between the starting and end of travel or ending positions and provides a selected position alarm when the position signal equals the calculated position signal.

In a further feature, the detector comprises a potentiometer and the marker is resiliently biased against the potentiometer. In one aspect of the potentiometer, a linear potentiometer is disposed along a predetermined length of and in parallel with the route of travel of the position marker.

In yet a further feature, the processor receives a desired rate of movement of the plunger driver or drive means, calculates a change in the position signal per unit of time which would occur at the desired rate, and provides an alarm if the rate of movement represented by the change in the position signal differs from the desired rate.

In a preferred embodiment, a processor contains data relating to the particular syringe in use which includes the end of travel position of the plunger of that syringe. The data also includes the volume per distance (milliliters/inch) characteristic of the syringe. A processor receives the operator's indication of the installed syringe type and the selection of infusion rate and calculates the rate of plunger movement to obtain that infusion rate with that syringe. The processor also determines the end of travel voltage to to be received from the potentiometer wiping contact which would indicate the end of travel position for this syringe. To perform this calculation, the processor recalls the stored end of travel position for the particular syringe and the particular response characteristic for the potentiometer, which may not be linear. The processor also determines the voltage for the near end of travel point, which in one embodiment is fixed at three minutes. The processor then periodically monitors the continuous output voltage from the potentiometer wiping contact, compares it against the

UNITED STATES PATENT AND TRADEMARK OFFICE
CERTIFICATE OF CORRECTION

PATENT NO. : 5,236,416
DATED : August 17, 1993
INVENTOR(S) : John D. McDaniel, James E. Gharib It is certified that error appears in the above-identified patent and that said Letters Patent is hereby corrected as shown below:

calculated near end of travel voltage and upon discovering equality, provides an alarm. The processor also provides an end of travel alarm when the wiping contact voltage equals the calculated end of travel voltage.

In accordance with another feature, data relating to a plurality of syringes having different sizes and manufacturers are stored in the processor so that it is possible to use a variety of different syringes in the pump and still have accurate near end of travel and end of travel alarms.

In the Detailed Description of the Preferred Embodiments:

Column 3, Line 64-65, change "particularly" to --particularity--.
Column 4, Line 64, change "V" to --$V_o$--.
Column 5, Line 4, change "this" to --This--.
Column 6, Line 10, change "lunger" to --plunger--.
Column 7, Line 5, change "measuring" to --measured--.
Column 7, Line 39, change "syring" to --syringe--.

In the Claims:
Column 9, Line 47, between "to" and "received," insert --be--.

Signed and Sealed this

Thirteenth Day of December, 1994

*Attest:*

BRUCE LEHMAN

*Attesting Officer*     *Commissioner of Patents and Trademarks*